United States Patent [19]  [11] 4,066,639
Weber et al.  [45] Jan. 3, 1978

[54] BENZENE-SULFONYL SEMICARBAZIDES AND PROCESS FOR PREPARING THEM

[75] Inventors: Helmut Weber, Frankfurt am Main; Karl Muth, Kelkheim, Taunus; Rudi Weyer, Frankfurt am Main; Walter Aumuller, Kelkheim, Taunus; Erich Haack, Heidelberg, all of Germany

[73] Assignee: Hoechst Aktiengesellschaft, Frankfurt am Main, Germany

[21] Appl. No.: 544,018

[22] Filed: Jan. 24, 1975

Related U.S. Application Data

[63] Continuation of Ser. No. 69,523, July 6, 1970, which is a continuation of Ser. No. 567,833, July 26, 1966, abandoned, which is a continuation-in-part of Ser. No. 542,723, May 6, 1965.

[30] Foreign Application Priority Data

May 6, 1965  Germany .................................. 45971

[51] Int. Cl.² .................. A61K 31/64; C07D 211/98; C07D 227/12; C07D 295/22
[52] U.S. Cl. ........................ 260/239 BF; 260/239 E; 260/239 A; 260/293.67; 260/293.68; 260/293.73; 260/294.8 F; 260/326.23; 260/332.2 C; 260/554; 424/244; 424/267; 424/274; 542/421

[58] Field of Search .................. 260/239 BF, 332.2 C, 260/554, 292, 293.73, 294.8 F, 326.3, 240 K, 239 A

[56] References Cited

U.S. PATENT DOCUMENTS 3,183,260  5/1965  Loev ........................................ 260/465
3,426,067  2/1969  Weber et al. ........................... 260/553

Primary Examiner—Alton D. Rollins
Attorney, Agent, or Firm—Curtis, Morris & Safford

[57] ABSTRACT

A benzene-sulfonyl semicarbazide of the formula

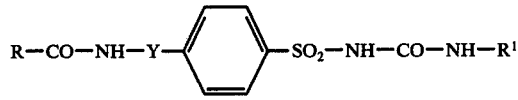

wherein R is such as phenyl and substituted phenyl, cyclohexyl or alkyl, Y is -CH$_2$CH$_2$- or

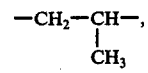

R$_1$ is alkylene-imino of 3 to carbon atoms which may also be substituted; a representative compound is 4-[4-(β-<2-methoxy-5-chloro-benzamido->-ethyl)-benzene-sulfonyl]-1,1-(γ,γ-dimethyl-pentamethylene)-semicarbazide.

5 Claims, No Drawings

BENZENE-SULFONYL SEMICARBAZIDES AND PROCESS FOR PREPARING THEM

This is a continuation, of application Ser. No. 69,523, filed July 6, 1970, which in turn is a continuation of Ser. No. 567,833, filed July 26, 1966 and now abandoned, which in turn is a continuation-in-part of application Ser. No. 542,723, filed May 6, 1965.

The present invention provides compounds of the formula

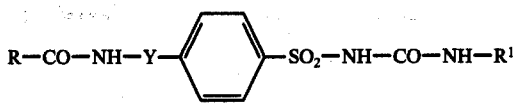

wherein

R a. represents a phenyl radical which may be substituted once, twice or three times by lower alkyl, lower alkenyl, lower alkoxy, lower alkenoxy, lower alkoxyalkoxy or halogen, furthermore by methylene-dioxy or trifluoromethyl, b. a thiophene radical which may be substituted once or twice by lower halogen, lower alkyl, lower alkoxy, lower alkenyloxy, lower alkoxyalkoxy, lower phenalkoxy or lower aryl, or by a polymethylene chain linked with its two ends to the thiophene radical, which chain contains from 3 to 4 carbon atoms, c. a furyl radical which may be substituted by methyl or halogen, d. a phenyl radical bound via an alkylene chain containing from 1 to 4 carbon atoms which may be branched and/or unsaturated and/or contain an oxygen atom instead of one $CH_2$-group, the phenyl radical containing, if desired, lower alkyl or lower alkoxy or halogen, e. a cyclohexyl or cyclohexenyl radical, f. an alkyl radical containing from 1 to 11 carbon atoms, Y represents a $-CH_2-CH_2-$ or

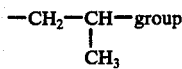

$R^1$ represents a. an alkylene-imino-radical containing from 3 to 7 carbon atoms wherein the alkylene chain may be substituted by 2 to 4 methyl groups or by alkyl or alkoxy containing up to 3 carbon atoms, or it may contain an endoalkylene group having from 1 to 3 carbon atoms and which may be substituted by lower alkyl or lower alkoxy or alkenyleneimino of 5 carbon atoms.

b. The radical

wherein $R_1$ and $R_2$ stand for lower alkyl, $R_2$ also representing benzyl, and the salts thereof, which are valuable medicaments which are distinguished by a strong and particularly long-lasting blood-sugar lowering activity.

The present invention further relates to a process for preparing acid benzenesulfonyl semicarbazides. As modes of preparation there may be mentioned the following:

a. Reaction of R-CO-NH-Y-substituted benzenesulfonamides, preferably in the form of their salts, with imino-carbamic acid esters, imino-thiocarbamic acid esters, or iminoureas containing as imino radical the group $R^1$-, b. reaction of hydrazines of the formula $R^1$-$NH_2$ or their salts with R-CO-NH-Y-substituted benzenesulfonyl isocyanates, benzenesulfonyl carbamic acid esters, benzenesulfonyl thiocarbamic acid esters, carbamic acid halides or ureas, c. reaction of R-CO-NH-Y-substituted benzenesulfochlorides with $R^1$-substituted ureas, d. hydrolysis of benzenesulfonyl-isosemicarbazide ethers, isothiosemicarbazide ethers or benzenesulfonyl-imino-parabanio acids, e. exchange of the sulfur atom for an oxygen atom, in benzenesulfonyl thiosemicarbazides of the formula

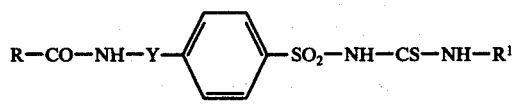

f. introduction of the radical R-CO- in one or several steps, into benzenesulfonyl semicarbazides of the formula

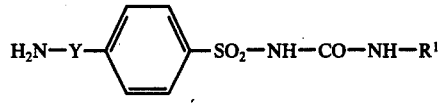

by acylation.

The benzenesulfonyl semicarbazides obtained may then be converted, if desired, into their salts by treatment with alkaline agents or with physiologically tolerable organic or inorganic acids.

As semicarbazides or imino-ureas for the syntheses mentioned under (a), there are suitable compounds of the formula $R^1$-NH-CO-$NH_2$ or acylated compounds of the formula $R^1$-NH-CO-NH-acyl wherein acyl represents an aliphatic or aromatic acid radical, preferably of lower molecular weight, or diphenyl semicarbazides of the formula $R^1$-NH-CO-N($C_6H_5$)$_2$, wherein the phenyl radicals may be substituted or may be linked to each other directly or by means of a bridge member, or N,N'-disubstituted carbohydrazides of the formula $R^1$-NH-CO-NH-$R^1$.

Especially suitable as benzenesulfonyl carbamic acid halides are the chlorides.

Furthermore, corresponding benzenesulfonyl ureas which may be unsubstituted at the terminal nitrogen atom, or substituted once or twice by alkyl or aryl groups, may be converted into the final products by reacting them with hydrazines of the formula $R^1$-$NH_2$, if desired, in the form of their salts. Instead of these benzenesulfonyl ureas there may be used the corresponding N-benzenesulfonyl-N'-acyl ureas or bis-(benzene-sulfonyl)-ureas. Said compounds may be treated with hydrazines of the formula $R^1NH_2$ and the salts obtained may be heated to elevated temperatures, preferably to at least 80° C.

The imino-carbamic acid esters or benzenesulfonyl carbamic acid esters mentioned as well as the corresponding thioesters contain in the ester component preferably an alkyl radical of low molecular weight or a phenyl radical.

The benzenesulfonyl isosemicarbazide ethers, -isothiosemicarbazide ethers or -parabanic acids used as starting materials, may be obtained by reacting corresponding isosemicarbazide ethers, isothiosemicarbazide ethers or parabanic acids with corresponding benzenesulfochlorides. Benzenesulfonyl isosemicarbazide ethers are also obtained, in the first place, by desulfurizing benzenesulfonyl thiosemicarbazides in methanolic solution. They are subsequently converted into benzenesulfonyl semicarbazides by hydrolysis.

Depending on the nature of the member R-CO-, in some cases, the one or the other of the previously described methods may prove unsuitable for preparing the individual compounds falling under the general formula, or at least will make it necessary for active groups to be protected. Such rare cases can easily be recognized by the expert, and there is no difficulty in successfully applying another one of the syntheses described.

As regards the reaction conditions, the embodiments of the process of the present invention may, in general, vary within wide limits and may be adapted to each individual case. For example, the reactions can be effected with the use of solvents, at room temperature or at an elevated temperature. As starting substances there are used, as one reactant, compounds containing a benzene radical substituted by the group R-CO-NH-Y-. As radical R may be mentioned, for example, the following groups:

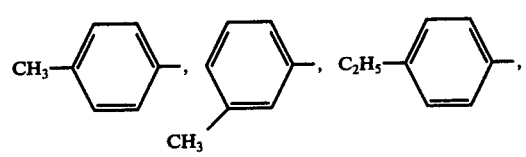

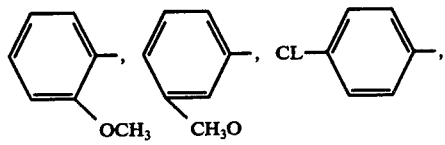

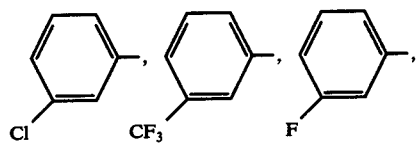

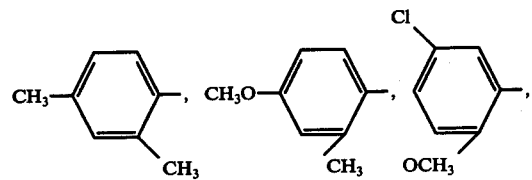

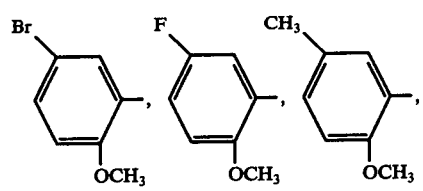

-continued

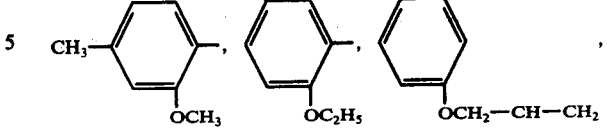

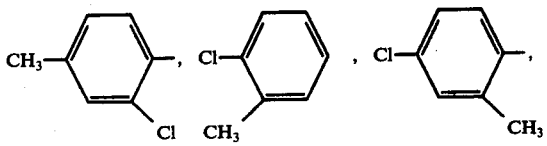

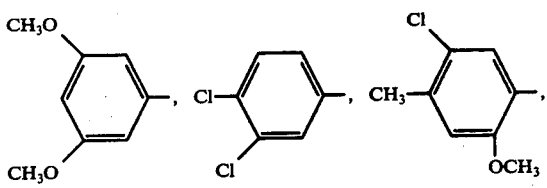

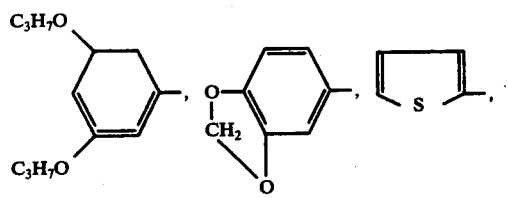

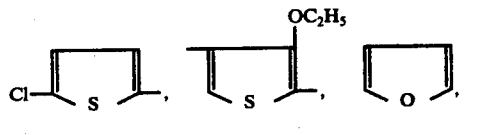

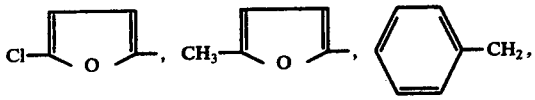

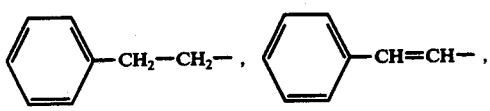

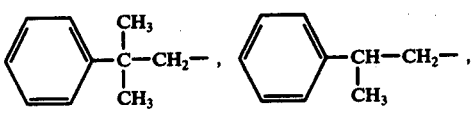

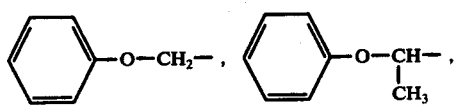

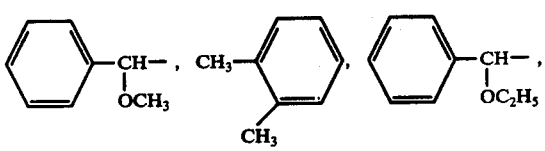

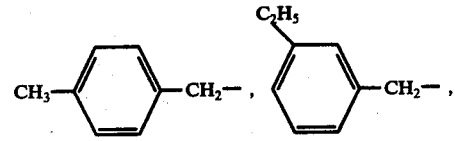

-continued

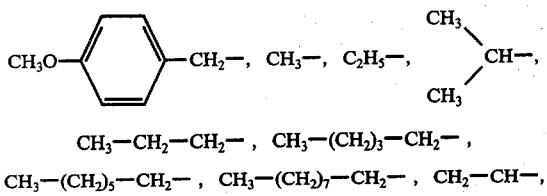

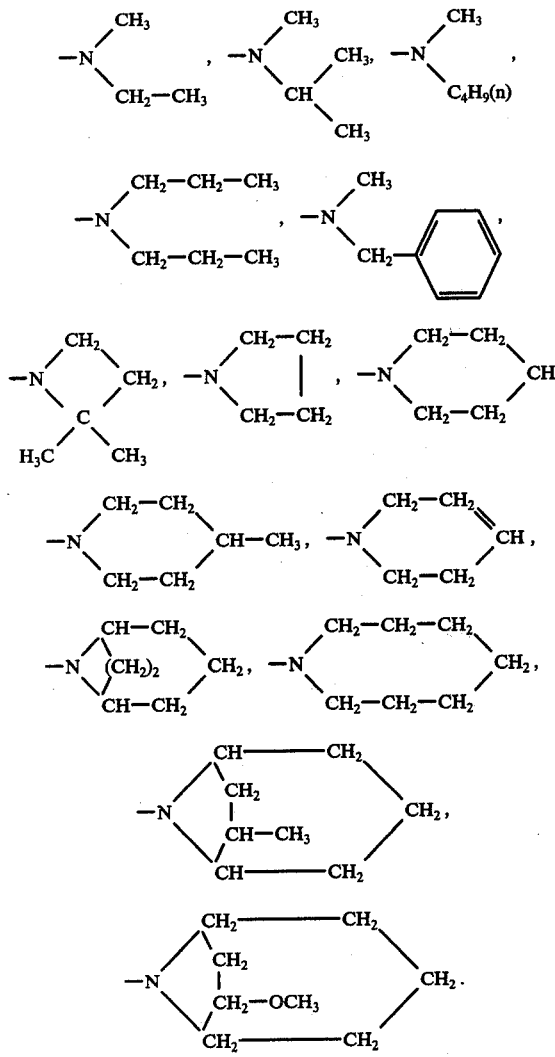

The sulfonyl-semicarbazide derivatives obtainable according to the present invention, are valuable medicaments which are distinguished by a strong and particularly long lasting action of lowering the blood sugar level. This applies, in particular, to such compounds in which R represents a phenyl radical carrying an alkoxy group in 2-position. The blood sugar lowering action of the products of the invention could be ascertained, for example, in rabbits, by administering the compounds in a dose of 10 mg/kg and by determining the blood sugar value, over a prolonged period of time, according to the known method of Hagedorn-Jensen. The following table comprises the blood sugar lowering activities of some of the compounds obtained according to the process of the present invention:

| Compound | Lowering of the blood sugar in rabbits after administering 10 mg/kg per os after hours | | | Limit amount causing lowering of the blood sugar level in rabbits mg/kg |
| --- | --- | --- | --- | --- |
| | 3 | 24 | 48 | |
| 4-[4-($\beta$-<$\beta$-phenyl-propionamido>-ethyl)-benzenesulfonyl]-1,1-pentamethylene-semi-carbazide | 26 % | 22 % | — | 0.15 |
| 4-[4-($\beta$-<2-Propoxy-benzamido>-ethyl-benzenesulfonyl]-1,1-($\gamma$-methyl-pentamethylene)-semicarbazide | 17 % | 42 % | — | 0.07 |
| 4-[4-($\beta$-<2-Methoxy-5-chlorobenzamido>-ethyl)-benzenesulfonyl]-1,1-pentamethylene-semicarbazide | 32 % | 20 % | — | 0.2 |
| 4-[4-($\beta$-<2-Methoxy-5-chlorobenzamido>-ethyl)-benzenesulfonyl]-1,1-hexamethylene-semicarbazide | 28 % | 22 % | 31 % | 0.06 |
| 4-[4-($\beta$-<2-Methoxy-4-chlorobenzamide>-ethyl)-benzenesulfonyl]-1,1-($\gamma$-methyl-pentamethylene)-semicarbazide | 26 % | 29 % | 7 % | 0.15 |
| 4-[4-($\beta$-<2-Methoxy-5-methyl-benzamido>-ethyl)-benzenesulfonyl]-1,1-($\gamma$-methyl-pentamethylene)-semicarbazide | 30 % | 35 % | — | 0.05 |
| 4-[4-($\beta$-<2-Methoxy-ethoxy-5-methyl-benzamido>-ethyl)-benzenesulfonyl]-1,1-($\gamma$-methyl-pentamethylene)-semicarbazide | 25 % | 31 % | — | 0.2 |
| 4-[4-($\beta$-<2-Methoxy-benzamido>-ethyl-benzenesulfonyl-1,1-pentamethylene-semicarbazide | 20 % | 7 % | — | 0.3 |

In contradistinction thereto, the N-(4-methyl-benzenesulfonyl)-N'-n-butyl-urea known as antidiabetic and used as medicament shows no lowering of the blood sugar level when administered in a dose of 25 mg/kg in a comparative test.

It is preferable to process the products of the present invention into orally administerable preparations which have blood sugar lowering action and which can accordingly be used in the treatment of diabetes mellitus; they can be employed as such or in the form of their salts or in the presence of substances causing salt formation. For such salt formation there can be used, for example, alkaline agents such as alkali metal hydroxides, alkaline earth metal hydroxides, alkali metal carbonates, alkaline earth metal carbonates, alkali metal bicarbonates and alkaline earth metal bicarbonates and physiologically tolerated acids. The pharmaceutical preparations are preferably in the form of tablets which contain, in addition to the compounds of the present invention, the usual adjuvants and carriers such as talc, starch, lactose, tragacanth, magnesium stearate and the like.

The following Examples serve to illustrate the present invention, but they are not intended to limit it thereto:

EXAMPLE 1 a. 4-[4-B-{3-chloro-benzamido}-ethyl)-benzenesulfonyl]-1.1-pentamethylene-semicarbazide 10 Grams of N-[4-(β-{3-chloro-benzamido}-ethyl)-benzenesulfonyl}-methyl-urethane (m.p. 173°–175° C) were suspended in 100 ml of dioxane and 2.8 grams of 1.1-pentamethylene-hydrazine were added while stirring. The mixture was heated to 120° – 130° C for an hour while the methanol formed during the reaction process, was distilling off together with a little amount of dioxane. When being cooled the 4-[4-(β-{3-chlorobenzamido}-ethyl)-benzenesulfonyl}-1.1-pentamethylene-semicarbazide formed precipitated in crystalline form and was purified by dissolving it in dilute ammonia and by subsequently precipitating it with dilute acetic acid. After recrystallization from methanol and dimethyl formamide, the semicarbazide melted at 229° – 231° C (decomposition).

In analogous manner there were obtained:

b. 4-[4-(β-{3-chloro-benzamido}-ethyl)-benzenesulfonyl]-1.1-hexamethylene-semicarbazide, m.p. 207° – 209° C (decomposition) (from methanol/dimethyl formamide) and c. 4-[4-(β-{3-chloro-benzamido}-ethyl)-benzenesulfonyl]-1-methyl-1-benzyl-semicarbazide, m.p. 112° – 114° C (decomposition) (from methanol/water);
from N-[4-(β-{4-chloro-benzamido}-ethyl)-benzenesulfonyl}methyl-urethane, m.p. 213° – 215° C, d. 4-[4-(β-{4-chloro-benzamido}-ethyl)-benzenesulfonyl]1.1-pentamethylene-semicarbazide, m.p. 220° – 223° C (decomposition) (from dimethyl formamide/water) and e. 4-{4-(β-{4-chloro-benzamido}-ethyl)-benzenesulfonyl]-1.1-hexamethylene-semicarbazide, m.p. 195° – 198° C (decomposition) (from dimethyl formamide/methanol);
from N-[4-(β-{4-fluoro-benzamido}-ethyl)-benzenesulfonyl]-methyl urethane, m.p. 194° – 196° C f. 4-[4-(β-{4-fluoro-benzamido}-ethyl)-benzenesulfonyl]-1.1-pentamethylene-semicarbazide, m.p. 238° – 240° C (decomposition) (from methanol/dimethyl formamide) and g. 4-[4-(β-{4-fluoro-benzamido}-ethyl)-benzenesulfonyl]-1.1-hexamethylene-semicarbazide, m.p. 208° – 210° C (decomposition) (from methanol/dimethyl formamide);
from N-[4-(β-{3-methyl-benzamido}-ethyl)-benzenesulfonyl]methyl-urethane, m.p. 200° – 202° C h. 4-[4-(β-{3-methyl-benzamido}-ethyl)-benzenesulfonyl]-1.1-pentamethylene-semicarbazide, m.p. 241° – 243° C (decomposition) (from methanol/dimethyl formamide) and i. 4-[β-{3-methyl-benzamido}-ethyl)-benzenesulfonyl]-1.1-hexamethylene-semicarbazide, m.p. 209° – 211° C (from methanol/dimethyl formamide);
from N-[4-(β-{2-methoxy-benzamido}-ethyl)-benzenesulfonyl]methyl-urethane, m.p. 174° – 176° C k. 4-[4-(β-{2-methoxy-benzamido}-ethyl)-benzenesulfonyl]-1.1-pentamethylene-semicarbazide, m.p. 157° – 159° C (from methanol), l. 4-[4-(β-{2-methoxy-benzamido}-ethyl)-benzenesulfonyl]-1.1-hexamethylene-semicarbazide, m.p. 155° – 157° C (from methanol) and m. 4-[4-(β-{2-methoxy-benzamido}-ethyl)-benzenesulfonyl]-1.1-tetramethylene-semicarbazide, m.p. 172° – 174° C (from methanol/dimethyl formamide);
from N-[4-(β-{3-methoxy-benzamido}-ethyl)-benzenesulfonyl]-methyl-urethane, m.p. 173° – 175° C n. 4-[4-(β-{3-methoxy-benzamido}-ethyl)-benzenesulfonyl]-1.1. pentamethylene-semicarbazide, m.p. 230° – 232° C (decomposition) (from methanol/dimethyl formamide; and o. 4-[4-(β-{3-methoxy-benzamido}-ethyl)-benzenesulfonyl]-1.1-hexamethylene-semicarbazide, m.p. 207° – 209° C (decomposition) (from methanol/dimethyl formamide);
from N-[4-(β-{2-allyloxy-benzamido}-ethyl)-benzenesulfonyl]-methyl-urethane, m.p. 145° – 148° C p. 4-[4-(β-{2-allyloxy-benzamido}-ethyl)-benzenesulfonyl]-1.1-pentamethylene-semicarbazide, m.p. 157° – 159° C (from methanol);
from N-[4-(β-{2-methoxy-5-methyl-benzamido}-ethyl)-benzenesulfonyl]-methyl-urethane, m.p. 175° – 177° C q. 4-[4-(β-{2-methoxy-5-methyl-benzamido}-ethyl)-benzenesulfonyl]-1.1-pentamethylene-semicarbazide, m.p. 176° – 178° C (decomposition) (from methanol);
from N-[4-(β-{β-phenyl-propionamido}-ethyl)benzenesulfonyl]methyl-urethane, m.p. 137° – 139° C r. 4-[4-(β-{β-phenyl-propionamido}-ethyl)-benzenesulfonyl]-1.1-pentamethylene-semicarbazide, m.p. 173° – 175° C (decomposition) (from methanol);
from N-[4-(β-{3-trifluoromethyl-benzamido}-ethyl)-benzenesulfonyl]-methylurethane, m.p. 178° – 180° C s. 4-[4-(β-{3-trifluoromethyl-benzamido}-ethyl)-benzenesulfonyl]-1.1-pentamethylene-semicarbazide, m.p. 209° – 211° C (decomposition) (from methanol/dimethyl formamide) and t. 4-[4-(β-{3-trifluoromethyl-benzamido}-ethyl)-benzenesulfonyl]-1.1-hexamethylene-semicarbazide, m.p. 201° – 202° C (from methanol/dimethyl formamide);
from N-[4-(β-{3-methoxy-thiophene-2-carbonamido}-ethyl)-benzenesulfonyl]-methyl-urethane, m.p. 226° – 228° C (decomposition)

u. 4-[4-(β-{3-methoxy-thiophene-2-carbonamido}-ethyl)-benzene-sulfonyl]-1.1-pentamethylene-semicarbazide, m.p. 202° – 204° C (from methanol/dimethyl formamide) and v. 4-[4-(β-{3-methoxy-thiophene-2-carbonamido}-ethyl)-benzenesulfonyl]-1.1-hexamethylene-semicarbazide, m.p. 181° – 182° C (from methanol/dimethyl formamide);
from N-[4-(β-{phenoxy-acetamido}-ethyl)-benzenesulfonyl]-methyl-urethane, m.p. 136° – 138° C w. 4-[4-(β-{phenoxy-acetamido}-ethyl)-benzenesulfonyl]-1.1-pentamethylene-semicarbazide, m.p. 150° – 151° C (from methanol), x. 4-[4-(β-{phenoxy-acetamido}-ethyl)-benzenesulfonyl]-1.1-hexamethylene-semicarbazide, m.p. 111° – 113° C (from methanol) and y. 4-[4-(β-{phenoxy-acetamido}-ethyl)-benzenesulfonyl]-1.1-(3-methyl-pentamethylene)-semicarbazide, m.p. 153° – 155° C (from methanol);
from N-[4-(β-{β-phenyl-propionamido}-ethyl)-benzenesulfonyl]-methyl-urethane, m.p. 142° – 144° C z. 4-[4-(β-{β-phenyl-propionamido}-ethyl)-benzenesulfonyl]-1.1-hexamethylene-semicarbazide, m.p. 148° – 150° C (from methanol), aa. 4-[4-(β-{β-phenyl-propionamido}-ethyl)-benzenesulfonyl]-1.1-tetramethylene-semicarbazide, m.p. 167° – 168° C (from methanol), ab. 4-[4-(β-{β-phenyl-propionamido}-ethyl)-benzenesulfonyl]-1-methyl-1-benzyl-semicarbazide, m.p. 158° – 160° C (from methanol) and ac. 4-[4-(β-{β-phenyl-propionamido}-ethyl)-benzenesulfonyl]-1.1-(3-methyl-pentamethylene)-semicarbazide, m.p. 180° – 182° C (from methanol);

from N-[4-(β-{cinnamoylamido}-ethyl)-benzenesulfonyl]-methyl-urethane, m.p. 198° – 200° C ad. 4-[4-(β-{cinnamoylamido}-ethyl)-benzenesulfonyl]-1.1-(3-methyl-pentamethylene)-semicarbazide, m.p. 198° – 200° C (from methanol/dimethyl formamide);

from N-[4-(β-{Δ3-tetrahydro-benzamido}-ethyl)-benzenesulfonyl]-methyl-urethane, m.p. 151° – 153° C ae. 4-[4-(β-{Δ3-tetrahydro-benzamido}-ethyl)-benzenesulfonyl]-1.1-hexamethylene-semicarbazide, m.p. 170° – 171° C (decomposition) (from methanol) and af. 4-[4-(β-{Δ3-tetrahydro-benzamido}-ethyl)-benzenesulfonyl]-1.1-(3-methyl-pentamethylene)-semicarbazide, m.p. 184° – 186° C (decomposition) (from methanol);

from N-[4-(β-{3-trifluoromethyl-benzamido}-ethyl)-benzenesulfonyl]-methyl-urethane, m.p. 178° – 180° C ag. 4-[4-(β-{3-trifluoromethyl-benzamido}-ethyl)-benzenesulfonyl]-1.1-(3-methyl-pentamethylene)-semicarbazide, m.p. 222° – 224° C (from methanol/dimethyl formamide);

from N-[4-(β-{3-fluorobenzamido}-ethyl)-benzenesulfonyl]-methyl-urethane, m.p. 184° – 186° C ah. 4-[4-(β-{3-fluorobenzamido}-ethyl)-benzenesulfonyl]-1.1-pentamethylene-semicarbazide, m.p. 210° – 212° C (decomposition) (from methanol/dimethyl formamide), ai. 4-[4-(β-{3-fluorobenzamido}-ethyl)-benzenesulfonyl]-1.1-hexamethylene-semicarbazide, m.p. 198° – 200° C (from methanol) and ak. 4-[4-(β-{3-fluorobenzamido}-ethyl)-benzenesulfonyl]-1.1-tetramethylene-semicarbazide, m.p. 200° – 202° C (from methanol/dimethyl formamide);

from N-[4-(β-{3-chlorobenzamido}-ethyl)-benzenesulfonyl]-methyl-urethane, m.p. 173° – 175° C al. 4-[4-(β-{3-chlorobenzamido}-ethyl)-benzenesulfonyl]-1.1-(1-methyl-pentamethylene)-semicarbazide, m.p. 210° – 211° C (from methanol/dimethyl formamide) and am. 4-[4-(β-{3-chlorobenzamido}-ethyl)-benzenesulfonyl]-1-methyl-1-isopropyl-semicarbazide, m.p. 176° – 177° C (from methanol/dimethyl formamide);

from N-[4-(β-{4-fluorobenzamido}-ethyl)-benzenesulfonyl]-methyl-urethane, m.p. 194° – 196° C an. N-[4-(β-{4-fluorobenzamido}-ethyl)-benzenesulfonyl]-1.1-(3-methyl-pentamethylene)-semicarbazide, m.p. 215° – 217° C (decomposition) (from methanol/dimethyl formamide);

from N-[4-(β-capronamido-ethyl)-benzenesulfonyl]-methylurethane, m.p. 113° – 115° C ao. 4-[4-(β-capronamido-ethyl)-benzenesulfonyl]-1.1-(3-methyl-pentamethylene)-semicarbazide, m.p. 163° – 165° C (from methanol);

from N-[4-(β-{3-ethoxy-thiophene-2-carbonamido}-ethyl)-benzenesulfonyl]-methyl-urethane, m.p. 163° – 165° C, ap. 4-[4-(β-{3-ethoxy-thiophene-2-carbonamido}-ethyl)-benzenesulfonyl]-1.1-pentamethylene-semicarbazide, m.p. 159° – 161° C (from methanol) and aq. 4-[4-(β-{3-ethoxy-thiophene-2-carbonamido}-ethyl)-benzenesulfonyl]-1.1-hexamethylene-semicarbazide, m.p. 152° – 153° C (from methanol);

from N-[4-(β-{3-methoxy-benzamido}-ethyl)-benzenesulfonyl]-methyl-urethane, m.p. 173° – 174° C, ar. 4-[4-(β-{3-methoxy-benzamido}-ethyl)-benzenesulfonyl]1.1-(3-methyl-pentamethylene)-semicarbazide, m.p. 237° – 239° C (decomposition) (from methanol/dimethyl formamide);

from N-[4-(β-{2-ethoxybenzamido}-ethyl)-benzenesulfonyl]-methyl-urethane, m.p. 172° – 174° C, as. 4-[4-(β-{2-ethoxy-benzamido}-ethyl)-benzenesulfonyl]-1.1-pentamethylene-semicarbazide, m.p. 153° – 154° C (from methanol), at. 4-[4-(β-{2-ethoxy-benzamido}-ethyl)-benzenesulfonyl]-1.1-hexamethylene-semicarbazide, m.p. 135° – 137° C (from methanol) and au. 4-[4-(β-{2-ethoxy-benzamido}-ethyl)-benzenesulfonyl]-1.1-(1-methyl-pentamethylene)-semicarbazide, m.p. 137° – 139° C (from methanol);

from N-[4-(β-{2-propoxy-benzamido}-ethyl)-benzenesulfonyl]-methyl-urethane, m.p. 159° – 161° C av. 4-[4-(β-{2-propoxy-benzamido}-ethyl)-benzenesulfonyl]-1.1-(3-methyl-pentamethylene)-semicarbazide, m.p. 171° – 173° C (from methanol/dimethyl formamide);

from N-[4-(β-{2-methoxy-5-chlorobenzamido}-ethyl)-benzene-sulfonyl]-methyl-urethane, m.p. 189° – 192° C, aw. 4-[4-(β-{2-methoxy-5-chlorobenzamido}-ethyl)-benzenesulfonyl]-1.1-pentamethylene-semicarbazide, m.p. 164° – 166° C (from methanol) and ax. 4-[4-(β-{2-methoxy-5-chlorobenzamido}-ethyl)-benzenesulfonyl]-1.1-hexamethylene-semicarbazide, m.p. 161° – 163° C (from methanol);

from N-[4-(β-{2-methoxy-4-chlorobenzamido}-ethyl)-benzenesulfonyl]-methyl-urethane, m.p. 178° – 180° C, ay. 4-[4-(β-{2-methoxy-4-chlorobenzamido}-ethyl)-benzenesulfonyl]-1.1-(3-methyl-pentamethylene)-semicarbazide, m.p. 177° – 179° C (from methanol);

from N-[4-(β-{2-methoxy-3-chlorobenzamido}-ethyl)-benzenesulfonyl]-methyl-urethane, m.p. 151° – 153° C, az. 4-[4-(β-{2-methoxy-3-chlorobenzamido}-ethyl)-benzenesulfonyl]-1.1-pentamethylene-semicarbazide, m.p. 173° – 175° C (from methanol);

from N-[4-(β-{3-ethoxy-benzamido}-ethyl)-benzenesulfonyl]-methyl-urethane, m.p. 165° – 167° C, ba. 4-[4-(β-{3-ethoxy-benzamido}-ethyl)-benzenesulfonyl]-1.1-pentamethylene-semicarbazide, m.p. 207° – 208° C (decomposition) (from methanol/dimethyl formamide), bb. 4-[4-(β-{3-ethoxy-benzamido}-ethyl)-benzenesulfonyl]-1.1-hexamethylene-semicarbazide, m.p. 177° – 179° C (from methanol/dimethyl formamide) and bc. 4-[4-(β-{3-ethoxy-benzamido}-ethyl)-benzenesulfonyl]-1.1-(3-methyl-pentamethylene)-semicarbazide, m.p. 224° – 226° C (decomposition) (from methanol/dimethyl formamide);

from N-[4-(β-{2-methoxy-5-methylbenzamido}-ethyl)-benzenesulfonyl]-methyl-urethane, m.p. 175° – 177°

C, bd. 4-[4-(β-{2-methoxy-5-methylbenzamido}-ethyl)-benzenesulfonyl]-1.1-hexamethylene-semicarbazide, m.p. 155° – 157° C (from methanol) and be. 4-[4-(β-{2-methoxy-5-methylbenzamido}-ethyl)-benzenesulfonyl]-1.1-(3-methyl-pentamethylene)-semicarbazide, m.p. 176° – 178° C (from methanol);
from N-[4-(β-{2-β-methoxy-ethoxy-benzamido}-ethyl)-benzenesulfonyl]-methyl-urethane, m.p. 123° – 125° C, bf. 4-[4-(β-{2-β-methoxy-ethoxy-benzamido}-ethyl)-benzenesulfonyl]-1.1-pentamethylene-semicarbazide, m.p. 143° – 145° C (from methanol) and bg. 4-[4-(β-{2-β-methoxy-ethoxy-benzamido}-ethyl)-benzenesulfonyl]-1.1-(3-methyl-pentamethylene)-semicarbazide, m.p. 157° – 159° C (from methanol);
from N-[4-(β-{2-ethoxy-5-chlorobenzamido}-ethyl)-benzenesulfonyl]-methyl-urethane, m.p. 203° – 205° C bh. 4-[4-(β-{2-ethoxy-5-chlorobenzamido}-ethyl)-benzenesulfonyl]-1.1-pentamethylene-semicarbazide, m.p. 163° – 165° C (from methanol) and bi. 4-[4-(β-{2-ethoxy-5-chloro-benzamido}-ethyl)-benzenesulfonyl]-1.1-hexamethylene-semicarbazide, m.p. 164° – 166° C (from methanol);
from N-[4-(β-{2-methoxy-3-methylbenzamido}-ethyl)-benzenesulfonyl]-methyl-urethane, m.p. 153° – 155° C bk. 4-[4-(β-{2-methoxy-3-methylbenzamido}-ethyl)-benzenesulfonyl]-1.1-(3-methyl-pentamethylene)-semicarbazide, m.p. 170° – 172° C (from methanol);
from N-[4-(β-{2-β-methoxy-ethoxy-5-methylbenzamido}-ethyl)-benzenesulfonyl]-methyl-urethane, m.p. 160° – 162° C, bl. 4-[4-(β-{2-βmethoxy-ethoxy-5-methylbenzamido}-ethyl)-benzenesulfonyl]-1.1-(3-methyl-pentamethylene)-semicarbazide, m.p. 151° – 153° C (from methanol);
from N-[4-(β-{3-chloro-phenoxy-acetamido}-ethyl)-benzenesulfonyl]-methyl-urethane, m.p. 121° – 123° C bm. 4-[4-(β-{3-chlorophenoxy-acetamido}-ethyl)-benzenesulfonyl]-1.1-(3-methyl-pentamethylene)-semicarbazide, m.p. 106° – 108° C (decomposition) (from methanol);
from N-[4-(β-{β-4-chlorophenyl-propionamido}-ethyl)-benzenesulfonyl]-methyl-urethane, m.p. 165° – 167° C bn. 4-[4-(β-{β-4-chlorophenyl-propionamido}-ethyl)-benzenesulfonyl]-1.1-pentamethylene-semicarbazide, m.p. 179° – 181° C (decomposition) (from methanol) and bo. 4-[4-(β-{β-4-chlorophenyl-propionamido}-ethyl)-benzenesulfonyl]-1.1-(3-methyl-pentamethylene)-semicarbazide, m.p. 163° – 165° C (from methanol);
from N-[4-(β-{β-3-chlorophenyl-propionamido}-ethyl)-benzenesulfonyl]-methyl-urethane, m.p. 128° – 130° C bp. 4-[4-(β-{β-3-chlorophenyl-propionamido}-ethyl)-benzenesulfonyl]-1.1-hexamethylene-semicarbazide, m.p. 161° – 163° C (from methanol) and bq. 4-[4-(β-{β-3-chlorophenyl-propionamido}-ethyl)-benzenesulfonyl]-1.1-(3-methyl-pentamethylene)-semicarbazide, m.p. 137° – 139° C (from methanol);
from N-[4-(β-{3.4-tetramethylene-thiophene-2-carbonamido}-ethyl)-benzenesulfonyl]-methyl-urethane, m.p. 194° – 196° C br. 4-[4-(β-{3.4-tetramethylene-thiophene-2-carbonamido}-ethyl)-benzenesulfonyl]-1.1-entamethylene-semicarbazide, m.p. 149° – 151° C (from methanol/dimethyl formamide) and bs. 4-[4-(β-{3.4-tetramethylene-thiophene-2-carbonamido}-ethyl)-benzenesulfonyl]-1.1(3-methyl-pentamethylene)-semicarbazide, m.p. 168° – 169° C (from methanol);
from N-[4-(β-{2-methoxy-3.5-dichlorobenzamido}-ethyl)-benzenesulfonyl]-urethyl-methane, m.p. 187° – 188° C bt. 4-[4-(β-{2-methoxy-3.5-dichlorobenzamido}-ethyl)-benzenesulfonyl]-1.1-(3-methyl-pentamethylene)-semicarbazide, m.p. 161° – 163° C (from methanol/dimethyl formamide);
from N-[4-(β-{2-methoxy-benzamido}-ethyl)-benzenesulfonyl]-ethyl-urethane, m.p. 168° C bu. 4-[4-(β-{2-methoxy-benzamido}-ethyl)-benzenesulfonyl]-(δ-dimethyl-pentamethylene)-semicarbazide, m.p. 155° – 157° C, bv. 4-[4-(β-{2-methoxy-benzamido}-ethyl)-benzenesulfonyl]-(1-isonorgranatanyl)-urea, m.p. 170° – 171° C, bw. 4-[4-(β-{2-methoxy-benzamido}-ethyl)-benzenesulfonyl]-1.1-(2.6-dimethyl-pentamethylene)-semicarbazide, m.p. 203° – 204° C, bx. 4-[4-(β-{2-methoxy-benzamido}-ethyl)-benzenesulfonyl]-1.1-(β-pentamethylene)-semicarbazide, m.p. 175° – 176° C, by. $N_1$-4-[4-(β-{2-methoxy-benzamido}-ethyl)-benzenesulfonyl]-$N_2$-[norgranatyl-(9)]-urea, m.p. 190° – 191° C, bz. $N_1$-4-[4-(β-{2-methoxy-benzamido}-ethyl)-benzenesulfonyl]-$N_2$-[nortropanyl-(8)]-urea, m.p. 213° – 214° C, ca. $N_1$-4-[4-(β-{2-methoxy-benzamido}-ethyl)-benzenesulfonyl]-$N_2$-(1.2.5.6-tetrahydropyridyl-1)-urea, m.p. 156° – 157° C.

In analoguous manner there were obtained from the corresponding acylamino-ethyl-benzenesulfonylmethyl-urethanes cb. 4-[4-(β-{2-methoxy-5-chlorobenzamido}-ethyl)-benzenesulfonyl]-1.1-(α-methyl-pentamethylene)-semicarbazide, m.p. 185° – 186° C, cc. 4-[4-(β-{2-methoxy-5-chlorobenzamido}-ethyl)-benzenesulfonyl]-1.1-(α,α-dimethyl-trimethylene)-semicarbazide, m.p. 135° C, cd. 4-[4-(β-{2-methoxy-5-chlorobenzamido}-ethyl)-benzenesulfonyl]-1.1-(β,β-dimethyl-trimethylene)-semicarbazide, m.p. 196° – 197° C, ce. 4-[4-(β-{2-methoxy-5-bromobenzamido}-ethyl)-benzenesulfonyl]-1.1-(β,β-dimethyl-trimethylene)-semicarbazide, m.p. 205° – 206° C, cf. 4-[4-(β-{2.5-dimethoxy-benzamido}-ethyl)-benzenesulfonyl]-1.1-(β,β-dimethyl-trimethylene)-semicarbazide, m.p. 198° – 199° C, cg. 4-[4-(β-{2-methoxy-5-fluorobenzamido}-ethyl)-benzenesulfonyl]-1.1-(β,β-dimethyl-trimethylene)-semicarbazide, m.p. 185° C, ch. 4-[4-(β-{2-methoxy-5-fluoro-benzamido}-ethyl)-benzenesulfonyl]-1.1-(β,β-dimethyl-pentamethylene)-semicarbazide, m.p. 115° C, ci. 4-[4-(β-{2-methoxy-5-chlorobenzamido}-ethyl)-benzenesulfonyl]-1.1-(β,β-dimethyl-pentamethylene)-semicarbazide, m.p. 186° C, ck. 4-[4-(β-{2-methoxy-5-bromobenzamido}-ethyl)-benzenesulfonyl]-1.1-(β,β-dimethyl-pentamethylene)-semicarbazide, m.p. 188° C, cl. 4-[4-(β-{2.5-dimethoxy-benzamido}-ethyl)-benzenesulfonyl]-1.1-(β,β-dimethyl-pentamethylene)-semicarbazide, m.p. 154°–155° C, cm. 4-[4-(β-{4-chlorobenzamido}-ethyl)-benzenesulfonyl]-1.1-(γ-methyl-pentamethylene)-semicarbazide, m.p. 198° - 200° C, cn. 4-[4-(β-{2-methoxy-benzamido}-ethyl)-benzenesulfonyl]-1.1-(β-methyl-tetramethylene)-semicarbazide, m.p. 161°–162° C, co. 4-[4-(β-{2-methoxy-benzamido}-ethyl)-benzenesulfonyl]-1.1-(α,α,α',α'-tetramethyl-pentamethylene)-semicarbazide, m.p.

cp. 4-[4-(β-{2-methoxy-5-chlorobenzamido}-ethyl)-benzenesulfonyl]-1.1-(β-methyl-pentamethylene)-semicarbazide, m.p. 167° - 168° C.

cq. 4-[4-(β-{2-methoxy-5-chlorobenzamido}-ethyl)-benzenesulfonyl]-1.1-(γ-ethyl-pentamethylene)-semicarbazide, m.p. 157° - 159° C, cr. 4-[4-(β-{2-methoxy-5-chloro-benzamido}-ethyl)-benzenesulfonyl]-1.1-(γ,γ-dimethyl-pentamethylene)-semicarbazide, m.p. 191° - 193° C, cs. 4-[4-(β-{2-methoxy-5-chlorobenzamido}-ethyl)-benzenesulfonyl]-1.1-(β-ethyl-pentamethylene)-semicarbazide, m.p. 180° - 181° C, ct. 4-[4-(β-{2-methoxy-5-bromobenzamido}-ethyl)-benzenesulfonyl]-1.1-(γ-ethyl-pentamethylene)-semicarbazide, cu. 4-[4-(β-{2-ethoxy-5-chlorobenzamido}-ethyl)-benzenesulfonyl]-1.1-(β,β-dimethyl-pentamethylene)-semicarbazide, cv. 4-[4-(β-{2-methoxy-5-fluorobenzamido}-ethyl)-benzenesulfonyl]-1.1-(γ,γ-dimethyl-pentamethylene)-semicarbazide, m.p. 160° - 162° C, cw. 4-[4-(β-{2-methoxy-4-chlorobenzamido}-ethyl)-benzenesulfonyl]-1.1-(γ,γ-dimethyl-pentamethylene)-semicarbazide, m.p. 166° - 167° C, cx. 4-[4-(β-{2-methoxy-5-bromobenzamido}-ethyl)-benzenesulfonyl]-1.1-(γ,γ-dimethyl-pentamethylene)-semicarbazide, m.p. 182° C, cy. 4-[4-(β-{2-ethoxy-5-chlorobenzamido}-ethyl)-benzenesulfonyl]-1.1-(γ,γ-dimethyl-pentamethylene)-semicarbazide, m.p. 162° - 165° C, cz. 4-[4-(β-{2.5-dimethoxy-benzamido}-ethyl)-benzenesulfonyl]-1.1-(γ,γ-dimethyl-pentamethylene)-semicarbazide, m.p. 170° - 171° C, da. 4-[4-(β-{2-methoxy-5-bromobenzamido}-ethyl)-benzenesulfonyl]-1.1-(γ-ethyl-pentamethylene)-semicarbazide, m.p. 145° - 146° C, db. 4-[4-(β-{2-methoxy-5-fluorobenzamido}-ethyl-benzenesulfonyl]-1.1-(γ-ethyl-pentamethylene)-semicarbazide, m.p. 167° C, dc. 4-[4-(β-{2.5-dimethoxy-benzamido}-ethyl-ethyl)-benzenesulfonyl]-1.1-(γ-ethyl-pentamethylene)-semicarbazide, m.p. 122° - 123° C, dd. 4-[4-(β-{2-methoxy-5-chlorobenzamido}-ethyl)-benzenesulfonyl]-1.1-(γ,γ-dimethyl-trimethylene)-semicarbazide, m.p. 196° - 197° C, de. 4-[4-(β-{2-methoxy-5-bromobenzamido}-ethyl)-benzenesulfonyl]-1.1-(γ,γ-dimethyl-trimethylene)-semicarbazide, m.p. 205° - 206° C, df. 4-[4-(β-{2.5-dimethoxy-benzamido}-ethyl)-benzenesulfonyl]-1.1-(γ,γ-dimethyl-trimethylene)-semicarbazide, m.p. 198° - 199° C, dg. 4-[4-(β-{2-methoxy-5-fluorobenzamido}-ethyl)-benzenesulfonyl]-1.1-(γ,γ-dimethyl-trimethylene)-semicarbazide, m.p. 185° C.

EXAMPLE 2

4-[4-(β-benzamido-ethyl)-benzenesulfonyl]-1.1-pentamethylenesemicarbazide a. 14.7 Grams of 4.4-diphenyl-1.1-pentamethylene-semicarbazide were suspended with 16.3 grams of the sodium salt of 4-(β-benzamido-ethyl)-benzenesulfonamide in 100 ml of dimethyl formamide and the whole was heated to 100° C for 3 hours. After cooling, the whole was diluted with water, the reaction mixture was rendered alkaline with ammonia and the diphenyl amine formed was removed by shaking it out three times with ether. The aqueous phase was filtered and acidified with glacial acetic acid. The 4-[4-(β-benzamido-ethyl)-benzenesulfonyl]-1.1-pentamethylene-semicarbazide precipitating in crystalline form, melted at 217° - 218° C after having been recrystallized from dimethyl formamide and water. In analogous manner there was obtained b. 4-[4-(β-benzamido-ethyl)-benzenesulfonyl]-1.1-hexamethylenesemicarbazide, m.p. 233°–236° C (from dimethyl formamide/water).

EXAMPLE 3

4-[4-(β-benzamido-ethyl)-benzenesulfonyl]-1.1-pentamethylene-semicarbazide a. 5.9 Grams of 1-pentamethyleneimino-parabanic acid were suspended in 240 ml of benzene. After addition of 3 grams of trimethyl amine the mixture was dissolved and 9.7 grams of 4-(β-benzamido-ethyl)-benzenesulfochloride were added while stirring. The whole was refluxed for 3 hours, then cooled and decanted from the smeary residue. This residue was digested with water in order to remove the triethylamine hydrochloride formed, and was made to recrystallize by trituration with alcohol and water. The 4-[4-(β-benzamido-ethyl)-benzenesulfonyl]-3-pentamethylene-imino-parabanic acid thus obtained was purified by boiling it with methanol and it melted at 228° C (decomposition).

b. 0.5 Gram of the parabanic acid derivative obtained in the manner described above, was heated with 5 ml of 1N sodium hydroxide solution on the steam bath for 10 minutes. After a little while the salt of 4-[4-(β-benzamido-ethyl)-benzenesulfonyl]-1.1-pentamethylene-semicarbazide crystallized out. It yielded the free compound m.p. 218° C by acidification with dilute acetic acid.

EXAMPLE 4

4-[4-(β-4-chloro-benzamido-ethyl)-benzenesulfonyl]-1.1-pentamethylene-semicarbazide 9.5 Grams of N-[4-(β-4-chloro-benzamido-ethyl)-benzenesulfonyl]-urea, m.p. 194° - 196° C, were refluxed at the boil in 100 ml of dioxane with 5 grams of N-amino-piperidine. After a limpid solution had been formed, the solvent was evaporated at reduced pressure, the residue was treated with about 1% ammonia, after filtration the filtrate was acidified with dilute acetic acid. The 4-[β-4-chlorobenzamido-ethyl)-benzenesulfonyl]-1.1-pentamethylene-semicarbazide which had precipitated, was recrystallized from water and dimethyl formamide and it melted at 220° - 223° C (decomposition).

EXAMPLE 5

4-[4-(β-{3-methyl-4-chlorobenzamido}-ethyl)-benzenesulfonyl]-1.1-pentamethylene-semicarbazide a. 16.8 Grams of 4-(β-{3-methyl-4-chloro-benzamido}-ethyl)-benzenesulfonamide sodium were heated to 180° C with 11.1 grams of 1.1.5.5-bis-pentamethylene-carbohydrazide, m.p. 178° C in a preheated oil bath for 10 to 15 minutes. The mixture became pasty and then solidified again. After having been cooled it was treated with water, after filtration the filtrate was acidified with acetic acid and the reaction product was recrystallized from methanol. The 4-[4-(β-{3-methyl-4-chlorobenzamido}-ethyl)-benzenesulfonyl]-1.1-pentamethylene-semicarbazide melted at 204° - 206° C.

In analogous manner there were obtained:
b. 4-[4-(β-{3-methyl-4-chlorobenzamido}-ethyl)-benzenesulfonyl]-1.1-tetramethylene-semicarbazide, m.p. 174° - 176° C (from methanol/water) and
from 4-(β-{αmethoxy-phenyl-acetamido}-ethyl)-benzenesulfonamide, m.p. 167° - 169°, and 1.1.5.5-bis-pentamethylenecarbohydrazide
c. 4-[4(β-{α-methoxy-phenylacetamido}-ethyl)-benzenesulfonyl]-1.1-pentamethylene-semicarbazide, m.p. 146° - 148° C.

EXAMPLE 6 a.
4-[4-(β-benzamido-ethyl)-benzenesulfonyl]-1.1-(γ-methyl-pentamethylene)-semicarbazide 0.01 mol of N-[4-(β-benzamido-ethyl)-benzenesulfonyl]-methyl-urethane were heated to 110° - 120° C while stirring, in 135 ml of toluene with 0.01 mol of γ-methyl-pentamethylene-hydrazine. The methyl alcohol forming was distilled off. After heating for 2 - 3 hours, the whole was allowed to cool and the residue was filtered off with suction; it was dissolved and reprecipitated from Na₂CO₃ and HCl. The 4-[4-(β-benzamido-ethyl)-benzenesulfonyl)-1.1-(γ-methyl-pentamethylene)-semicarbazide obtained melted at 212° C.

In analogous manner there were obtained:
b. 4-[p-(β-benzamido-ethyl)-benzenesulfonyl]-1-methyl-1-isopropyl-semicarbazide, m.p. 204° C,
c. 4-[p-(benzamido-ethyl)-benzenesulfonyl]-1.1-(β-methoxypentamethylene)-semicarbazide, m.p. 212° C.
d. 4-[p-(β-benzamido-ethyl)-benzenesulfonyl]-1.1-(γ-isopropoxy-pentamethylene)-semicarbazide, m.p. 210° C.
e. N₁-[p-(β-benzamido-ethyl-benzenesulfonyl[-N₄-[noratanyl-(9)]-urea, m.p. 229° - 230° C,
f. 4-[4-(β-acetamido-ethyl)-benzenesulfonyl]-1.1-pentamethylene-semicarbazide, m.p. 203° C,
g. 4-[4-(β-acetamido-ethyl)-benzenesulfonyl]-1.1-(γ-methyl-penetamethylene)-semicarbazide, m.p. 187° - 189° C.

EXAMPLE 7

4-[4-(β-benzamido-ethyl)-benzenesulfonyl]-1.1-pentamethylene-semicarbazide 0.013 Mol of 4-[4-(γ-amino-ethyl)-benzenesulfonyl]-1.1-pentamethylene-semicarbazide prepared by hydrolysis of 4-[4-(β-acetylamino-ethyl)-benzenesulfonyl]1.1-penetamethylene-semicarbazide, m.p. 198° - 199° C, was heated to 35° C in 15 ml of chloroform with 0.024 ml of pyridine and 0.013 ml of benzoyl chloride for 6 hours. The residue was filtered off with suction and dissolved and re-precipitated from Na₂CO₃ and HCl. This compound melted at 216° - 218° C.

EXAMPLE 8 a.
4-[4-(β-2-methoxy-benzamido-ethyl)-benzenesulfonyl]-1.1-pentamethylene-semicarbazide 0.01 Mol of 4-[4-(β-amino-ethyl)-benzenesulfonyl]-1.1-pentamethylene-semicarbazide were dissolved in 0.01 mol of 2N NaOH and 0.01 mol of 2-methoxy-benzoyl chloride was added dropwise while stirring. For complete reaction the whole was heated to 40° C for 2 hours. The substance which had precipitated was filtered off with suction and the residue was dissolved and reprecipitated from Na₂CO₃ and HCl. The substance melted at 156° C.

In analogous manner there were obtained:
4-[4-(β-trimethyl-acetamido-ethyl)-benzenesulfonyl]-pentamethylene-semicarbazide, m.p. 187° - 189° C,
c. 4-[4- (β-3'-toluylamido-ethyl)-benzenesulfonyl]-1.1-(γ-methyl-pentamethylene)-semicarbazide, m.p. 234° - 235° C,
d. 4-[4-(β-3'-chloro-benzamido-ethyl)-benzenesulfonyl]-1.1-(γ-methyl-pentamethylene)-semicarbazide, m.p. 223° - 224° C.

EXAMPLE 9 a.
4-[4-(β-2-methoxy-benzamido-ethyl)-benzenesulfonyl]-1.1-(γ-methyl-pentamethylene)-semicarbazide 0.01 Mol of 4-[4-(β-amino-ethyl)-benzenesulfonyl]-1.1-(γ-methyl-pentamethylene)-semicarbazide, m.p. 187° - 189° C, being prepared by hydrolysis of 4-[4-(β-acetylamino-ethyl)-benzenesulfonyl]-1.1-(γ-methyl-pentamethylene)-semicarbazide, was added to 10 ml of pyridine and 0.01 mol of 2-methoxy-benzoyl chloride was added dropwise. While heating, the reaction took place. The substance was allowed to stand for 12 hours and was then heated on the steam bath for 30 minutes. After having been cooled it was poured onto ice, the precipitate was filtered off with suction, dissolved and reprecipitated from Na₂CO₃ and HCl. The pure substance melted at 154° C.

In analogous manner there were obtained:
b. 4-[4-(β-5'-chloro-2-methoxybenzamido-ethyl)-benzenesulfonyl]-1.1-(β-methyl-pentamethylene)-semicarbazide, m.p. 165° - 168° C,
c. 4-[4-(β-3'-methoxy-thiophene-2-carbamido-ethyl)-benzenesulfonyl]-1.1-(β-methyl-pentamethylene)-semicarbazide, m.p. 177° - 177° C,
d. 4-[4-(β-2'-ethoxy-benzamido-ethyl)-benzensulfonyl]-1.1-(γ-methyl-pentamethylene)-semicarbazide, m.p. 169° - 171° C,
e. 4-[4-(β-2'-methoxy-benzamido-ethyl)-benzenesulfonyl]-1.1-(γ-ethyl-pentamethylene)-semicarbazide, m.p. 160° C, with sintering, m.p. 166° C.

We claim:
1. The compound 4-[4-(β-{2-methoxy-5-chloro-benzamido}-ethyl)-benzene-sulfonyl]-1,1-(γ,γ-dimethyl-pentamethylene)-semicarbazide or its physiologically tolerable salt.
2. The compound 4-[4-(β-{2-methoxy-5-chlorobenzamido}-ethyl)-benzenesulfonyl]-1,1-(γ-methyl-pentamethylene)-semicarbazide or its physiologically tolerable salt.

3. The compound 4-[4-(β-{2-methoxy-5-chlorobenzamido}-ethyl)-benzenesulfonyl]-1,1-hexamethylene-semicarbazide or its physiologically tolerable salt.

4. The compound 4-[4-(β-{2-methoxy-5-chlorobenzamido}-ethyl)-benzenesulfonyl]-1.1-(γ-ethyl-pentamethylene)-semicarbazide or its physiologically tolerable salt.

5. The compound 4-[4-(β-{2-methoxy-5-bromobenzamido}ethyl)-benzenesulfonyl]-1.1-(γ,γ-dimethyl-pentamethylene)-semicarbazide or its physiologically tolerable salt.

* * * * *

UNITED STATES PATENT AND TRADEMARK OFFICE
CERTIFICATE OF CORRECTION

PATENT NO. : 4,066,639
DATED : January 3, 1978
INVENTOR(S) : Weber et al.

It is certified that error appears in the above-identified patent and that said Letters Patent are hereby corrected as shown below:

In the Heading, Item [63], line 4, "May 6, 1965" should be --April 15, 1966--;

Item [57], line 6 of the Abstract, "3 to carbon atoms" should read --3 to 7 carbon atoms--;

Column 1, line 8, "May 6, 1965" should be --April 15, 1966--;

Column 1, line 41, "$-CH_2-Ch_2-$" should be--- $-CH_2-CH_2-$ --;

Column 2, line 17, "...parabanio..." should be --...parabanic...--;

Column 4, line 5, the formula

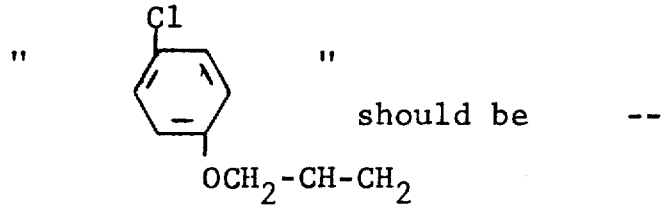

Column 4, line 12, the formula

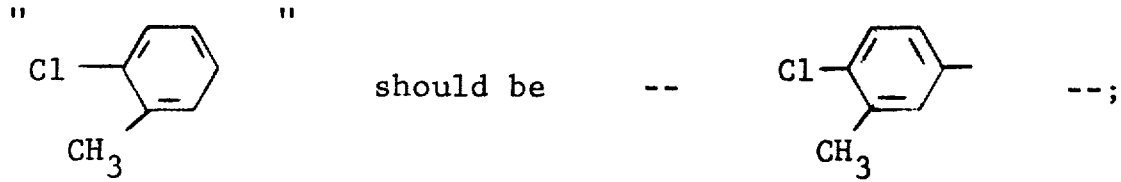

UNITED STATES PATENT AND TRADEMARK OFFICE
CERTIFICATE OF CORRECTION

PATENT NO. : 4,066,639
DATED : January 3, 1978
INVENTOR(S) : Weber et al.

It is certified that error appears in the above-identified patent and that said Letters Patent are hereby corrected as shown below:

Column 4, line 25, the formula

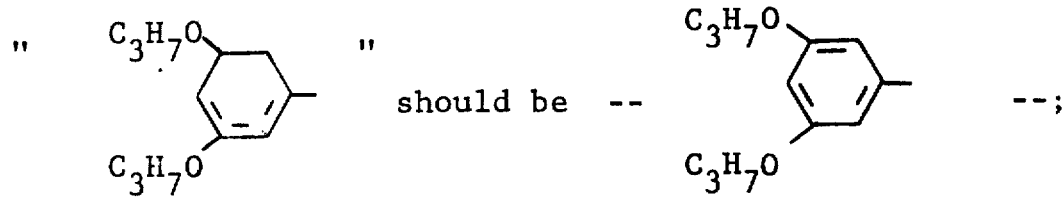

Column 4, line 35, the formulae

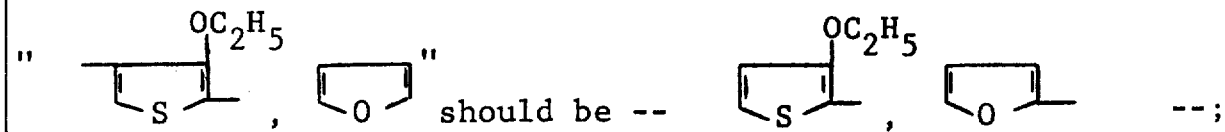

Column 4, line 39, "-CH$_2$," should be -- -CH$_2$-, --;

Column 4, line 58, the formula

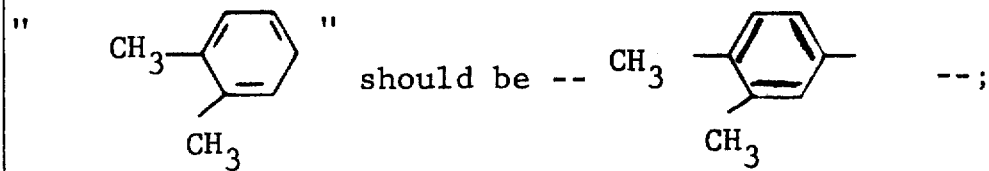

Column 5, line 9, "CH$_2$-CH-" should be --CH$_2$=CH- --;

Column 5, line 17, in the second formula, "-CH$_2$" should be -- -CH$_2$- --;

UNITED STATES PATENT AND TRADEMARK OFFICE
CERTIFICATE OF CORRECTION

PATENT NO. : 4,066,639
DATED : January 3, 1978
INVENTOR(S) : Weber et al.

It is certified that error appears in the above-identified patent and that said Letters Patent are hereby corrected as shown below:

Column 5, line 40,

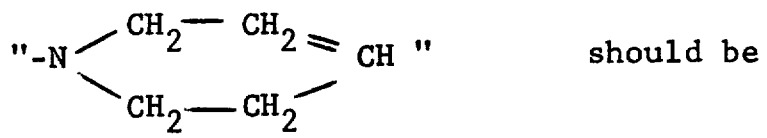   should be

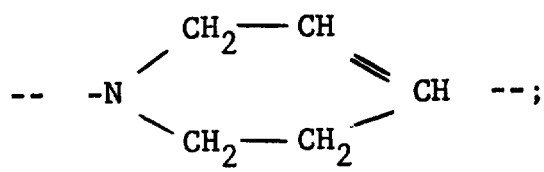 --;

UNITED STATES PATENT AND TRADEMARK OFFICE
CERTIFICATE OF CORRECTION

PATENT NO. : 4,066,639
DATED : January 3, 1978
INVENTOR(S) : Weber et al.

It is certified that error appears in the above-identified patent and that said Letters Patent are hereby corrected as shown below:

Column 5, line 55,

"
$$-N\begin{matrix} CH_2 \!-\!\!-\!\!- CH_2 \\ \diagdown \phantom{x} CH_2 \diagup \\ | \\ \diagup CH_2\!-\!OCH_3 \diagdown \\ CH_2 \!-\!\!-\!\!- CH_2 \end{matrix}CH_2$$
"

should be $$-N\begin{matrix} CH \!-\!\!-\!\!- CH_2 \\ \diagdown \phantom{x} CH_2 \diagup \\ | \\ \diagup CH\!-\!OCH_3 \diagdown \\ CH \!-\!\!-\!\!- CH_2 \end{matrix}CH_2$$

.

Signed and Sealed this

Eighth Day of August 1978

[SEAL]

Attest:

RUTH C. MASON
Attesting Officer

DONALD W. BANNER
Commissioner of Patents and Trademarks